US00RE35390E

United States Patent [19]

Smith

[11] E Patent Number: Re. 35,390

[45] Reissued Date of Patent: Dec. 3, 1996

[54] PRESSURE RELIEVING DEVICE AND PROCESS FOR IMPLANTING

[76] Inventor: Stewart G. Smith, Cloud Farm, Nine Gates Rd., Yorklyn, Del. 19736

[21] Appl. No.: 393,156

[22] Filed: Feb. 17, 1995

Related U.S. Patent Documents

Reissue of:

[64] Patent No.: 4,946,436
Issued: Aug. 7, 1990
Appl. No.: 437,840
Filed: Nov. 17, 1989

U.S. Applications:

[63] Continuation of Ser. No. 170,664, Dec. 16, 1993, abandoned, which is a continuation of Ser. No. 925,726, Aug. 4, 1992, abandoned.

[51] Int. Cl.[6] ..... A61M 5/00; A61F 2/14

[52] U.S. Cl. ..... 604/8; 623/4

[58] Field of Search ..... 604/8–10, 289, 604/294; 623/4

[56] References Cited

U.S. PATENT DOCUMENTS

| | | | |
|---|---|---|---|
| 4,037,604 | 7/1977 | Newkirk | 604/9 |
| 4,457,757 | 7/1984 | Molteno | 604/294 |
| 4,521,210 | 6/1985 | Wong | 604/8 |
| 4,634,418 | 1/1987 | Binder | 604/8 |
| 4,722,724 | 2/1988 | Schocket | 604/8 |
| 4,750,901 | 6/1988 | Molteno | 604/8 |
| 4,787,885 | 11/1988 | Binder | 604/8 |
| 4,936,825 | 6/1990 | Ungerleider | 604/8 |

*Primary Examiner*—Mary Beth Jones
*Attorney, Agent, or Firm*—Herbert M. Wolfson

[57] ABSTRACT

This invention involves a porous device for implantation in the scleral tissue of the eye to relieve the intraocular pressure of glaucoma and a method for surgically implanting the device.

8 Claims, 1 Drawing Sheet

PRESSURE RELIEVING DEVICE AND PROCESS FOR IMPLANTING

Matter enclosed in heavy brackets [ ] appears in the original patent but forms no part of this reissue specification; matter printed in italics indicates the additions made by reissue.

*This application is a continuation of Serial No. 08/170,664, filed Dec. 16, 1993, now abandoned, which is a continuation of 07/925,726 filed Aug. 4, 1992, now abandoned, which is a reissue of 07/437,840, filed Nov. 17, 1989, now U.S. Pat. No. 4,946,436.*

FIELD OF INVENTION

This invention relates to the drainage of aqueous humour from eyes in the course of relieving eye disorders. Specifically, the invention relates to an implant which, when permanently affixed to or implanted in a specific area of the eye, will provide such drainage efficiently, for longer periods than heretofore accomplished, and, in short, will provide relief and prevent (or at least postpone) the adverse ultimate effects of glaucoma.

BACKGROUND OF THE INVENTION

The eyeball is composed of three basic layers: (1) the sclera. (2) the middle layer and (3) the retina.

The sclera is the outer layer of the eyeball. It consists of tough, white tissue that serves as the supporting framework of the eye. At the front of the eye, the sclera is continuous with the clear, transparent cornea through which light enters the eye. Behind the cornea is a small space, the anterior chamber, which contains a clear watery fluid called the aqueous humour.

The middle layer is composed of three parts: (1) the choroid. (2) the ciliary muscle, and (3) the iris. The choroid lies behind and to the sides of the eyeball making up about 80% of the middle layer. It contains most of the blood vessels that nourish the eye.

Toward the front of the eyeball, the choroid becomes the ciliary muscle. This muscle is connected by fibers to the lens, keeping the lens in place and controlling its shape.

At the very front, the middle layer becomes the iris, a thin curtain of tissue in front of the lens. A round opening in the iris, whose size is controlled by muscles in the iris, is called the pupil.

In simple terms, the cornea refracts light through the anterior chamber and then through the pupil, the entrance aperture of the eye to the lens. The lens serves to focus the refracted light through the vitreous chamber containing the vitreous humour onto the retina, the rear surface of the eye.

Normally the fluid within the eye, the aqueous humour, is produced by the-ciliary body and migrates through the pupil into the anterior chamber, the small space behind the cornea. From this chamber, the liquid migrates through the trabecular meshwork and into the aqueous veins which form fluid collection channels beneath the conjuctiva, the latter covering the front of the eyeball except for the cornea.

When the aqueous, migration, described above, is insufficient to relieve the build-up of intra-ocular pressure, glaucoma results. This pressure build-up is usually due to one or more obstructions in the trabecular meshwork. Unless controlled, the high pressures associated with glaucoma ultimately leads to permanent damage of the optic nerve, the nerve formed from the sensitive fibers of the retina.

The object of the present invention is to provide a device that can be implanted permanently, simply and effectively to permit substantially normal migration of fluid out of the anterior chamber of the eye and, thus, avoid the abnormal build-up of intra-ocular pressure. Another object is to provide the implant in a manner that will also avoid excessive migration of fluid that would lead to collapse of the anterior chamber with its accompanying complications.

PRIOR ART

U.S. Pat. No. 4,457,757, issued Jul. 3, 1984 to A. C. B. Molteno, involves the use of at least two ridged bodies anchored to the sclera with two tubular extensions, one communicating through the sclera to the anterior chamber to drain the aqueous humour out of the eyeball.

U.S. Pat. No. 4,750,901, issued Jun. 14, 1988, to A. C. B. Molteno, recognized a problem that arose with his earlier device (as described in U.S. Pat. No. 4,457,757). In the first few days after insertion of the earlier device, the pressure within the eye tends to fall to an unacceptably low level "which may result in surgical complications which damage sight". This fall in pressure is due to excessive absorption of the aqueous humour by the patient's Tenon capsule, a smooth layer of tissue that covers the scleral plate when it is sutured to the eye. This later patent discloses the use of a subsidiary ridge in the upper surface the scleral plate that provides, with a portion of the Tenon's tissue, a small cavity where aqueous humour is drained initially and, thus, the aqueous humour can only be partially absorbed by the small area of Tenon's tissue exposed.

U.S. Pat. No. 4,634,418, issued Jan. 6, 1987, to P. S. Binder, involves the implantation of a seton constructed of a hydrogel in the anterior chamber of the eye to alleviate intra-ocular pressure. Once implanted, the seton acts as a wick to transfer aqueous humour from the anterior chamber to the space under the conjunctiva without allowing bacteria to ingress into the eye. Implantation is made after the removal of a rectangular-sized piece of cornea, Schalbe's line and a portion of the trabecular meshwork.

U.S. Pat. No. 4,722,724, issued Feb. 2, 1988, to S. Schocket, involves the use of an implant that includes two connected tubes or a tube connected to a band. One tube is located in the anterior chamber and the other tube or band is located around the orbit of the eye. To prevent hypotony, a destructible value is located at the end of the tube inserted with the interior chamber to control the pressure of the aqueous humour flowing from the chamber.

U.S. Pat. No. 4,787,885, issued Nov. 29, 1988 to P. S. Binder, is a continuation of an application that was a continuation-in-part of the application that resulted in U.S. Pat. No. 4,634,418. This patent, like its predecessor, also involves the removal of a rectangular-sized piece of cornea, Schwalbe's line and a portion of the trabecular meshwork to accomodate a seton; and the seton permits migration of the aqueous humour from the anterior chamber to the area beneath the conjunctiva (the external covering of the eye).

In both patents, the inventor achieves fluid flow to the exterior of the sclera into a space created beneath the conjunctiva and the accompanying Tenon's tissue that covers the scleral plate, i.e. outside the main body of the eye. Since these areas are particularly agressive in healing, the reduction in intra-ocular pressure is short-lived; the space created beneath the conjunctiva and the tenon tissue tends to collapse and prevent further migration of the fluid from the anterior chamber with the consequent pressure increase, characteristic of glaucoma.

The object of the present invention is to provide a means and method for treating the excessive intra-ocular pressure characteristic of glaucoma in a manner which will not be defeated by the subsequent healing process i.e. in a manner that will provide the patient with relief for several years. A further object is to help avoid other problems such as collapse of the anterior chamber, penetration of scar tissue over the trabecular meshwork, which tend to occur in the immediate post operative period with the conventional glaucoma surgery (trabeculotomy) disclosed in the prior art.

SUMMARY OF THE INVENTION

The invention involves an implant that is biocompatible with the tissue of the eye and allows fluid to migrate from the anterior chamber into the coarsely woven fibers of the sclera, thus by-passing the obstructed trabecular meshwork but, instead of leaving the body of the eye, exiting into the outer layer of the eyeball, the sclera. The normal pressure of fluid in the sclera serves to control the flow from the anterior chamber in a way that disastrous collapse of the chamber is prevented. Further, by not creating a space to accept fluid beneath the conjunctiva and the associated Tenon's tissue, the aggressive healing of these areas is not effective in recreating the excessive intra-ocular pressure in the anterior chamber.

Basically, this invention involves substituting a material that is composed of small pores of similar size or larger than a healthy trabecular meshwork in an area almost adjacent to the area of the troubled trabecular meshwork, i.e. close to where the sclera meets the cornea. In this manner, an area of relatively small pores within the implant, is placed within the relatively large pores of the sclera.

Specifically, the device for relieving intraocular pressure comprises a body portion and wall portions in substantially hexahedral form; at least the body portion is composed of a biocompatible porous hydrogel material. The device is adapted to be implanted within the scleral tissue of the eye with at least one edge of the device at an opening of, with no substantial extension into the anterior chamber adjacent to the area where the sclera makes the transition into the clear cornea of the eye. The pores of the body portion are of such size and quantity as to permit drainage of fluid from the anterior chamber to the scleral tissue without collapse of the anterior chamber. The wall portions have at least one extension on at least one wall portion for anchoring the device securely in position.

The implant is made from a hydrogel or other material which is biocompatible with the tissue of the eye. Such hydrogel material may have a water content ranging anywhere from about 30% to about 80%. Typically, such materials comprise silicones, acrylic polymers and/or fluorocarbon polymers or the like. The implant is shaped to retain its position once it is implanted within the eye and to provide sufficient surface area to accomodate the migration of the aqueou humour in a controlled manner, i.e. enough migration to reduce intra-ocular pressure but not enough to cause collapse of the chamber.

The invention will be more clearly understood by referring to the drawings and the description which follow.

THE DRAWINGS

DETAILED DESCRIPTION OF THE INVENTION

Figure 1:
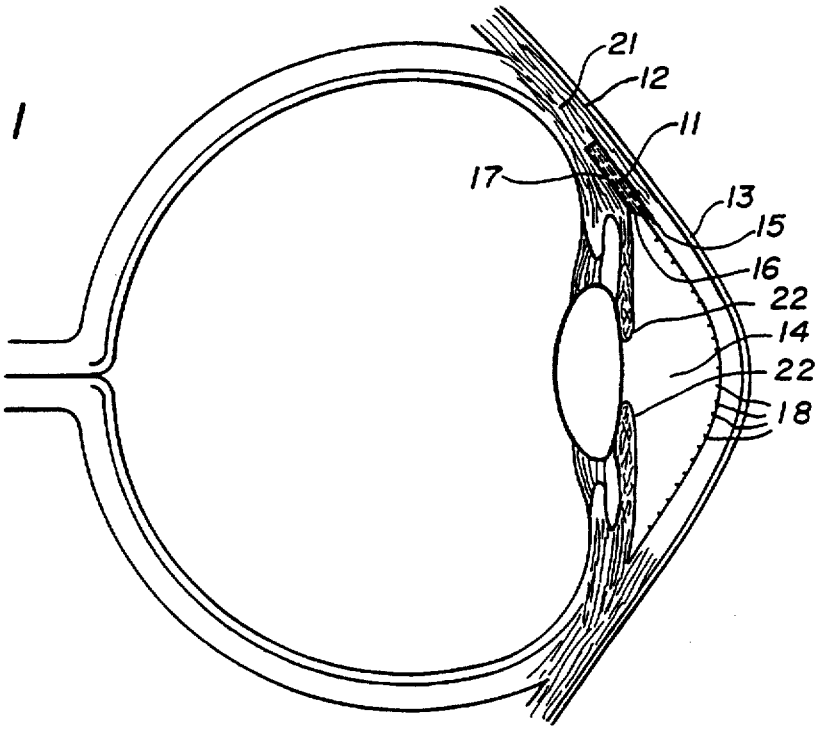
FIG. 1 is a cross-sectional view of the eye showing one embodiment of the invention implanted therein.
Figure 2:
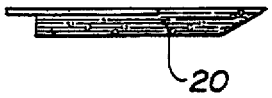
FIG. 2 is a side view of that embodiment of the invention.
Figure 3:
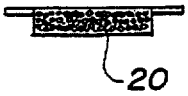
FIG. 3 is a front view of that embodiment.
Figure 4:
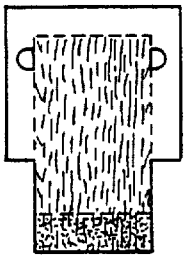
FIG. 4 is a plan or top view of that emobodiment.

In the first embodiment, the overall shape of the device 11 is a hexahedral structure having a substantially rectangular cross-section as shown in FIG. 1, approximately 6 mm in length, 3 mm in width, and ½ mm in depth. The device 11 is designed to be placed in a pocket made in the sclera 12 as seen in FIG. 1 in the following manner. An incision is made in the sclera, 2 mm from the limbus of the eye. A rectangular flap is raised into the clear cornea 13. The overall thickness of this flap is approximately ⅓ mm. Following the same incision technique, another flap of sclera 12 is raised underneath the previously made flap but extending into clear cornea 13. This block of sclera is then excised by entering the anterior chamber 14 at the anterior wound edge 15 (just as the sclera 12 makes the transition into clear cornea, 13). The aqueous fluid would then be able to enter this space through an opening; 16, 4½ mm in length, 1 mm in width, and ½ mm in depth. (Since the cornea follows a curve, the tissue excised would be triangular when viewed from the side.)

The implant 11 is then placed in this pocket created in the sclera 12 with the anterior portion of the device anchored in the lamellar shelf 17 previously created in the clear cornea 13. It should be noted that by anchoring the device in the lamellar shelf rather than extending the device into the anterior chamber, contact with the endothelial cells 18 along the interior surface of the cornea is avoided. Such contact would result in the death of these cells and the loss of corneal function.

Small lamellar dissections (1 mm in size) are created in the posterior wall, medial wall and lateral wall of the sclera 12. Using the embodiment of the device containing flanges, the flanges 19 (or extensions integral with the device) are placed within these lamellar dissections. By sliding the device 11 anteriorly, it becomes firmly anchored in the previously prepared corneal lamellar shelf 17. If necessary, it can be further secured by suturing the device to assure maintenance of its position. The first scleral flap is then sutured back into position. The sclera 12 with the implant 11 in position would be of approximately the same thickness as before the procedure.

Fluid would then exit the anterior chamber 14 through the incision under the flap and to the implanted device 11. It would then enter the implant 11 which would allow it access to three vertical walls of sclera because of the porous nature of the interior 20 of the implant. The coarsely woven fibers of the vertically cut sclera 12 would then allow the fluid to exit into the tissue 21 of the sclera 12.

Figure 5:
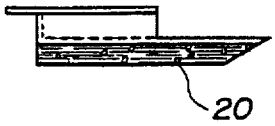
FIG. 5 is a side view of another emobodiment of the invention.
Figure 6:
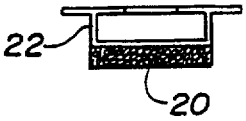
FIG. 6 is a front view of that other embodiment.
Figure 7:
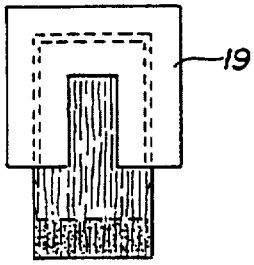
FIG. 7 is a plan view of that other embodiment.

The other embodiment shown in FIGS. 5, 6 and 7 consists of a similar basic implant 11 having similar dimensions but with a thin flange 19 (⅛ mm) around the base of the implant on all four sides. The flange would project 1 mm from the sides that would be in contact with the sclera only and about ½ mm for the side which would project into a raised flange. This raised flange is attached by a 1 mm extension 22 of the vertical walls of the portion of the implant in contact with the sclera. This extension is approximately ⅛ mm thick. Attached perpendicularly to this extension is the flange 19. The point of attachment is at the mid section of the flange. The flange is ⅛ mm thick and 2 mm wide. The posterior section is 7 mm in length and the two sides are 2½ mm in length.

This embodiment is implanted in a similar fashion to the previously described implant with the following modifications. 1. The initial scleral flap would be ½ mm. 2. A block of sclera would not be excised. 3. A lamellar dissection would be performed at the base of the flap for approximately 1 mm. 4. After the opening into the anterior chamber is created, the implant is placed into position sliding the posterior flange into the previously formed space from the lamellar dissection. The scleral flap is then placed back into its previous position and underneath the superior flange. This superior flange would overlie the incision into the sclera to create a flap of 1 mm on each side except for the furthermost anterior aspect (which would not be covered by Tenon's tissue since it does not insert as far anteriorly as the conjunctiva). The scleral flap is then sutured into position through the superior flange.

This embodiment would help prevent ingrowth of Tenon's tissue into the incision and would be firmly anchored into position. It also would allow access to vertically cut edges of sclera in the same manner as the previous embodiment.

A further modification of the device of the invention involves the particular method by which the fluid from the anterior chamber travels to the sclera. This modification would involve the use of a meshwork of fibers *26* to allow rapid flow of fluid through the spaces *28* between the fibers. The meshwork of fibers *26* being made of a biocompatible material would be flexible. The meshwork would allow fluid flow to the vertically cut edges of the implant and the sclera.

Another way to achieve porosity would be through a system of channels *30* through the implant. A variety of patterns could be cut so as to achieve high fluid flow through the implant to the vertically cut edges. For example, a fan shaped system *32* of drilled holes or a grid pattern of drilled holes from front to back or an interlocking pattern drilled from side to side, etc. could be used. The purpose and design are such that fluid could pass through, as described above, and the implant would resist collapse from the imposed pressure.

A typical operation for inserting the preferred embodiment of the invention follows: After retrobulbar anesthesia, the superior rectus muscle is placed on a four O silk bridal suture. Following this, a conjunctival flap is raised starting at the superior rectus and working forward to This is then reflected back to the cornea. Cautery is used to obtain hemostasis and to outline the location of the placement for the implant. A rectangular area, 5 mm by 3 mm, is outlined using a 64 Beaver blade. A small groove is made on the sclera side to half the depth of the sclera. This is grasped at one corner and the flap is dissected anteriorly until the rectangular flap is completely raised in the clear cornea. At this point a 75 blade is used to make a stab incision into the anterior chamber of the eye and a 1 by 4 mm section of the cornea and trabecular meshwork are excised en bloc.

Using a lamellar dissecting blade, attention is turned to the posterior aspect of the bed of the rectangular flap. Further dissection at the base is carried posteriorly for approximately 0.5 millimeter. The implant is then placed into position in this bed with the inferior posterior flap laid into the groove that has just been created on the posterior aspect of the bed. The anterior portion is in direct communication with the anterior chamber. The scleral flap is then laid over this implant and tucked in underneath the superior flanges that are present. If necessary, a portion of the scleral flap can be excised so that the sclera lays down smoothly over the implant. The implant is then sutured to the sclera on both sides with a 10-O nylon suture through the fixation holes in the superior flange. The conjunctival tissue is then sutured back together with a 6-O-plain gut running suture.

What is claimed is:

1. A device for relieving intraocular pressure comprises a body portion *and wall portions in the form of a hexahedron; at least the body portion* composed of a biocompatible porous material; said device adapted to be implanted within the scleral tissue of the eye with at least one edge of the device at an opening of, with no substantial extension into, the anterior chamber and adjacent to the area where the sclera makes the transition into clear cornea of the eye; the pores of the body portion are of such size and quantity as to permit drainage of fluid from the anterior chamber to the scleral tissue without collapse of the anterior chamber.

2. A device as in claim 1 wherein [one face of the hexahedron is] *said body portion has a first surface, said first surface of said body portion being* sloped to overlie the opening into the anterior chamber to direct fluid from the anterior chamber into the body portion of the device.

3. A device as in claim 1 wherein [at least one edge of one wall portion of the device] at least one edge of [one wall portion] *the top surface* of the device is extended for anchoring the device in position.

4. A device as in claim 1 wherein the *three* edges of [three wall portions of] the *top surface of the* device, other than [an] *the* edge at the opening of the anterior chamber, are extended for anchoring the device in position.

5. A device as in claim 1 wherein a thin flange extends from four sides of the base of the device, the flange at the posterior side of the device being raised and held in position by extensions of the vertical walls of said device [four sides of the base of device, the flange at the posterior side of the device being raised and held in position by extensions of the vertical walls of said device.]

6. A method for reducing intraocular pressure comprising the steps of:

creating a scleral flap by making an incision in the sclera substantially adjacent to the limbus of the eye;

excising a block of sclera by making a second incision into the sclera underneath the previously produced scleral flap but extending into the cornea and entering the anterior chamber at substantially the area where sclera becomes cornea to provide a pocket in the sclera and a shelf in the cornea [ and to provide a window providing direct fluid contact with the anterior chamber of the eye];

[providing a device for relieving intraocular pressure, said device comprising a body portion composed of a biocompatible porous material, said body portion comprising a first end portion and a second end portion, said body portion defining pores therethrough, said pores being of such size and quantity as to permit drainage of fluid from the anterior chamber to the scleral tissue without collapse of the anterior chamber]; and placing [said device for relieving intraocular pressure] *the hexahedrally shaped device of claim 1* in said pocket of the sclera [whereby said first end] *with the anterior* portion of said device [is] positioned in said shelf of the cornea [such that said first end portion is adjacent said window and is in direct fluid contact with the anterior chamber without extending substantially into the anterior chamber and whereby said second end portion is] *with the remaining portions of the device* positioned within the sclera.

*7. A device for relieving intraocular pressure comprising a body portion constructed of a biocompatible material having flow passages therein; said flow passages selected from the group consisting of pores, openings, channels and spaces between fibers in a meshwork of fibers; said device having a substantially uniform cross-section adapted to be fitted within the scleral tissue of the eye at an area adjacent an opening of, with no substantial extension into, the anterior chamber of the eye at a first position adjacent to the area of the eye where the sclera makes the transition into clear cornea of the eye; and extending to a second position within the scleral tissue of the eye, the distance between said first and second positions defining the length of the body portion through which fluid can flow, said length being approximately six (6) millimeters; said flow passages being of such size and quantity as to permit drainage of fluid from the anterior chamber to the scleral tissue without collapse of the anterior chamber.*

*8. A method for reducing intraocular pressure within the anterior chamber of an eye, said method comprising the following steps*

*a. creating a scleral flap by making an incision in the sclera of the eye substantially adjacent to the limbus of the eye;*

*b. excising a block of scleral tissue by making a second incision into the sclera underneath the previously produced scleral flap but extending into the cornea and entering the anterior chamber at substantially the area where sclera becomes cornea to provide a pocket in the sclera and a shelf in the cornea, c. placing a device for relieving intraocular pressure, said device comprising a body portion constructed of a biocompatible material; and having flow passages therein; said device having a first end portion and a second end portion with said flow passages therebetween; and*

*d. the device being placed in said pocket of the sclera with said first end portion of said device positioned in said shelf of the cornea whereby said first end portion of said body portion is in direct fluid contact with the anterior chamber of the eye without substantial extension into the anterior chamber of the eye and with the second end portion of said device positioned within the sclera of the eye to permit drainage of fluid from the anterior chamber into the scleral tissue without collapse of the anterior chamber.*

* * * * *